US007776322B2

(12) United States Patent
Kochanek et al.

(10) Patent No.: US 7,776,322 B2
(45) Date of Patent: Aug. 17, 2010

(54) MODIFIED VIRAL VECTOR PARTICLES

(76) Inventors: Stefan Kochanek, Maienweg 84, 89081 Ulm (DE); Florian Kreppel, Straubstrasse 10, 89081 Ulm (DE)

(*) Notice: Subject to any disclaimer, the term of this patent is extended or adjusted under 35 U.S.C. 154(b) by 0 days.

(21) Appl. No.: 11/120,155

(22) Filed: May 2, 2005

(65) Prior Publication Data

US 2006/0035378 A1 Feb. 16, 2006

Related U.S. Application Data

(60) Provisional application No. 60/601,902, filed on Aug. 16, 2004.

(51) Int. Cl.
*A61K 48/00* (2006.01)
*C12N 7/06* (2006.01)
*C12N 15/00* (2006.01)

(52) U.S. Cl. .................... 424/93.2; 435/238; 435/320.1

(58) Field of Classification Search ................ 424/93.2; 435/238, 320.1
See application file for complete search history.

(56) References Cited

U.S. PATENT DOCUMENTS

2003/0099619 A1* 5/2003 Wickham et al. .......... 424/93.2
2003/0152553 A1 8/2003 Little et al. ................ 424/93.2
2003/0219459 A1 11/2003 Bachmann et al. ....... 424/199.1

FOREIGN PATENT DOCUMENTS

| | | |
|---|---|---|
| WO | WO 95/06056 | 3/1995 |
| WO | WO 98/44143 | 10/1998 |
| WO | WO 99/39734 | 8/1999 |
| WO | WO 00/12738 | 3/2000 |
| WO | WO 2004/076627 | 9/2004 |

OTHER PUBLICATIONS

Wang et al. Chem. Biol. 9:813-819; 2002.*
Romanczuk et al. Hum.Gene Ther. 10:2615-2626; 1999.*
Lai et al. DNA Cell Biol. 21:895-913; 2002.*
Greber, U. Rev. Med. Virol. 8:213-222, 1998.*
Chatterji et al., "Chemical conjugation of heterologous proteins on the surface of cowpea mosaic virus," *Bioconjugate Chem.* 15:807-813, 2004.
Fisher et al., "Polymer-coated adenovirus permits efficient targeting and evades neutralizing antibodies," *Gene Ther.*, 8(5):341-348, 2001.
Greber et al., "The role of adnocirus protease on virus entry into cells," *EMBO J.*, 15(8):1766- 1777, 1996.
Jörvall and Philipson, "Limited proteolysis and a reactive cysteine residue define accessible regions in the native conformation of the adenovirus hexon protein," *Eur. J. Biochem.*, 104:237-247, 1980.
Krishnaswami et al., "Icosahedral Virus particles as polyvalent carbohydrate display platforms," *Chem. Bio. Chem.* 4:1348-1351, 2003.
Stubenrauch et al., "Conjugation of an antibody Fv fragment to a virus coat protein: cell-specific targeting of recombinant polyomavirus-like particles," *Biochem. J.*, 356(Pt.3):867-873, 2001.
Wang et al., "Icosahedral virus particles as addressable nanoscale building blocks," *Angew. Chem. Int. Ed.* 41:459-462, 2002.
Wang et al., "Natural supramolecular building blocks. Cystein-added mutants of cowpea mosaic virus," *Chem. Biol.*, 9(7):813-819, 2002.
Francis et al., "Pegylation of cytokines and other therapeutic proteins and peptides: the importance of biological optimisation of coupling techniques," *International Journal of Hematology*, 68:1-18, 1998.
O'Riordan et al., "Pegylation of adenovirus with retention of infectivity and protection from neutralizing antibody in vitro and in vivo," *Human Gene Therapy*, 10:1349-1358, 1999.
Romanczuk et al., "Modification of an adenoviral vector with biologically selected peptides: a novel strategy for gene delivery to cells of choice," *Human Gene Therapy*, 10:2615-2625, 1999.
Kreppel et al., "A novel platform for chemical modification of adenovirus vector capsids based on reactive cysteines," *Mol. Ther.* ,9(1):5252, 2004. (Abstract).
Kreppel et al., "Combined genetic and chemical capsid modifications enable flexible and efficient de- and retargeting of adenovirus vectors," *Mol. Ther.* 12:107-117, 2005.
Schmidt, "Untersuchungen von Varianten des Polyomavirus-Hullproteins VP1 im Hinblick auf gentherapeutische Anwendunge [Analyses of variants of the Polyomavirus-Envelope Protein VP1 with regard to its application in gene therapy]," Doctoral Thesis presented to the Faculty of Mathematics, Natural Sciences of the Martin-Luther University, Halle-Wittenberg, May 16, 2000 (Partial English Translation).

* cited by examiner

*Primary Examiner*—Fereydoun G Sajjadi
(74) *Attorney, Agent, or Firm*—Fulbright & Jaworski

(57) ABSTRACT

This invention relates to viral vector particles, including capsid proteins with an attachment site for the specific chemical modification of the vector particles. Furthermore, the invention relates to procedures for the production of these viral vector particles. Furthermore, the invention relates to the use of these viral vector particles as a therapeutic, prophylactic or diagnostic means in humans and primates as well as other vertebrates like cattle, pigs, birds, fish, or rodents.

12 Claims, 2 Drawing Sheets

Ad1Cys
+ SPA-PEG
+ Tf-Mal

Ad1Cys
+ SPA-PEG

Ad1Cys
unmodified 100 pMOI 1000 pMOI 5000 pMOI

MODIFIED VIRAL VECTOR PARTICLES

This application claims benefit of priority to U.S. Provisional Application Ser. No. 60/601,902 filed Aug. 16, 2004, the entire contents of which are hereby incorporated by reference.

FIELD OF THE INVENTION

This invention relates to viral vector particles, including capsid proteins with an attachment site for the specific chemical modification of the vector particles. Furthermore, the invention relates to procedures for the production of these viral vector particles. Furthermore, the invention relates to the use of these viral vector particles as a therapeutic means.

BACKGROUND OF THE INVENTION

Viral vector particles such as adenovirus gene transfer vectors are used in vitro and in vivo in order to transfer genes into living cells for therapeutic purposes (gene therapy), for vaccination purposes and for functional studies. Adenoviral vector particles can be produced in high titers, their genome is highly stable and they have the capability to transduce proliferating and resting cells. One can distinguish between different types of adenovirus vector particles: for example there are so-called first generation vector particles (the E1 functions are deleted), second generation vector particles (additional deletion of E2 and/or E4 functions), high-capacity vector particles (deletion of most or all viral genes). Furthermore, there are also replication-competent adenovirus vector particles (commonly referred to as oncolytic adenoviruses), which are for example used in tumor therapy. Additionally there are also chimeric adenovirus vector particles, whereby capsids of different serotypes are being combined. One example is the substitution of the natural serotype 5 Fiber protein with a Fiber protein derived from a different serotype such as for example serotype 17 or serotype 9.

Adenoviruses were found in numerous species. More than 50 different human serotypes are known, for example Ad12 (Subgenus A), Ad3 and Ad7 (Subgenus B), Ad2 and Ad5 (Subgenus C), Ad8 (Subgenus D), Ad4 (Subgenus E), Ad40 (Subgenus F) (Wigand, 1986). Apart from being detected in human beings, adenoviruses were also found in most vertebrates including chimpanzees, cattle, pigs, mice and chicken. Most of the currently used vector particles for gene transfer are based on adenovirus type 5 (Ad5), although numerous laboratories are also working on the development of vector particles which are either based on a different human-pathogenic serotype or which were isolated from chimpanzees, cattle or another species.

The transduction of cells by Ad5 vector particles takes place via at least two receptors. Initially the vector particles bind with the Knob domain of the capsid protein Fiber to the Coxsackie and Adenovirus receptor (CAR). This interaction induces minor structural modifications in the vector particle which allow an interaction of the penton base protein of the vector particles with the integrins of the cell surface. Finally, there is an integrin-mediated uptake of the vector particles into the cell via receptor-mediated endocytosis. During uptake of the vector particles and in the early endosome a regulated, gradual disassembly of the vector particles takes place by substantial participation of the viral cysteine protease p23 and which is completed after leaving the early endosome and upon entering the nucleus. This process depends on the redox status of the cysteine protease p23. The DNA is carried to the nuclear pores in this way, is being released from the capsid remnants and finally translocated into the nucleus as a last step in the transduction process.

One of the limitations of adenoviral vector particles for gene transfer is that many tissues which represent a possible target for therapeutic gene transfer with adenovirus vector particles do not express the CAR-receptor and/or the necessary integrins. Adenovirus vector particles only poorly transduce such tissues even when high doses are applied. Therefore, therapeutic gene transfer is not possible. As examples, the cells of the hematopoietic system, most types of tumor cells, neuronal cells, muscle cells and endothelial cells can be mentioned here. In addition, the use of adenovirus vectors derived from adenovirus isolated from a species other than the one to be treated with the vector might be hampered due to poor transduction efficiencies.

A further limitation of adenovirus vector particles for gene transfer becomes apparent after systemic administration of vector particles into the bloodstream. On the one hand there are interactions with cellular or non-cellular blood components such as erythrocytes, platelets, complement or antibodies which are able to neutralize the vector particles or which are responsible for toxic reactions, and on the other hand there is also CAR-/integrin-mediated uptake into tissues which are not the intended target of the vector particle application. Equally limiting are vector particle interactions with cellular components of the immune system such as Kupffer cells which can lead to neutralization of the vector particles and can induce undesirable side effects.

The current standard of knowledge includes two different strategies whereby one can try to modify the tropism of virus vector particles or one can prevent the undesirable interactions of virus vector particles with, e.g., antibodies.

The first strategy, subsequently referred to as "genetic strategy" consists of a defined genetic modification of solvent-exposed areas of various capsid proteins (e.g., Fiber, protein IX, Hexon). Here one tries to enhance gene transfer into target cells by genetic insertion of peptide ligands into for example the Knob domain of the Fiber protein of Ad5 (Dmitriev, 1998). This genetic strategy shows many concrete disadvantages: (i) there is a significant limitation regarding the size of the ligands to be used, because large ligands interfere with the correct folding of the modified capsid proteins; (ii) it is not possible to predict whether the production of vector particles even after genetic insertion of small ligands is possible because correct protein folding can be disturbed. Furthermore, the structure and biological function of peptide ligands in the context of vector capsid proteins are not predictable and small peptide ligands usually show only limited affinity for the target receptor on the target cell's surface; (iii) substantial genetic modifications, required for successful tropism modification of the adenovirus vector particles, lead to a low yield in vector particle production; (iv) for the production of genetically modified vector particles with new tropism, especially when additional mutations eliminate the interaction with CAR, it is necessary to generate a new production cell line for every ligand—this is a considerable obstacle and inhibits efficient screening for potential ligands; and (v) all genetic procedures are by nature limited to protein/peptide ligands for the tropism modification—peptides containing non-natural amino acids cannot be applied. In addition, other substances than proteins, e.g., steroids, other aromatic compounds or carbohydrates and others cannot be applied.

A second strategy, subsequently referred to as "chemical strategy" consists of unspecific chemical modifications of all solvent-exposed vector particle capsid proteins. Here one uses chemical reactions in order to couple ligands to naturally occuring primary amino groups on the surface of the vector particles. This procedure unspecifically modifies all capsid proteins and is being carried out under oxidative conditions at or slightly above physiological pH (7,4-8,5). (EP0694071B1 and Fisher, 2001) The limitations of the chemical strategy are: (i) the chemical reactions with activated ester groups to form amide bonds or with aldehydes to generate Schiff bases which were used so far, are targeted towards amino groups on the surface of all capsid proteins—single capsid proteins can therefore not specifically be modified; (ii) due to missing specificity for certain capsid proteins, most ligands show a significant cross linking of capsid proteins while coupling—consequently, the natural and for an efficient gene transfer necessary disassembly of the vector particles can severly be impaired after cellular uptake of the modified vector particles; and (iii) the chemical coupling of ligands by activated esters on primary amino groups of the capsid surface under formation of stable amide bonds or by aldehyde groups under formation of Schiff bases is not reversible under biological conditions. Through this, endosmolytic vector particle functions, i.e., functions for the endosomal escape after receptor-mediated endocytosis can be inhibited and can lead to low gene transfer efficiency.

The use of cysteine residues for thiol-specific coupling is a procedure which is being used in various applications. For example Stubenrauch et al. published a paper which describes the coupling of recombinant antibodies to Polyoma-Virus-like Particles (VLP) with the aid of a cysteine residue as an attachment site (Stubenrauch, 2001). A further example for the use of cysteine residues for the formation of covalent bonds is U.S. 2003-219459 A1, which also describes a procedure for the coupling of recombinant proteins to VLPs, whereby the attachment site on the VLP is not a cysteine residue, but the coupling partner is bearing a cysteine residue for attachment to the VLP. Importantly, as opposed to viral vector particles as described here, VLPs are synthetically manufactured particles and are assembled in vitro, i.e., outside living cells and their assembly is totally independent of cellular elements such as transcription factors or chaperone systems und totally independent of cellular processes such as DNA replication. Therefore, they are e.g. not capable of productive infections meaning that they are not able to replicate and multiply under certain conditions.

Recently, Wang et al. described mutants of the Cowpea Mosaic Virus (CPMV), which carry genetically modified solvent-exposed cysteine residues on the capsid surface (Wang, 2002). These mutants were solely produced in order to provide supra-molecular building blocks for chemical synthesis. The production of the plant virus mutant was achieved only under stringent observance of reducing conditions. Deviation from these conditions led to irreversible aggregation and precipitation through formation of interparticular disulfide bridges. The particles of these virus mutants simply serve as an element for chemical synthesis and biological functions were not analyzed.

Upon application of reducing reagents and alkylating reagents on Ad5 virus particles not only the genetically introduced solvent-exposed thiols will be modified, but also the viral cysteine protease p23 of the adenovirus (Greber, 1996). Greber et al. showed for the wildtype adenovirus serotype 2 that after reducing the virus particles by Dithiothreitol (DTT) and subsequent thiolspecific alkylation/esterification by various reagents such as N-ethylmaleimide (NEM) or iodoacetamid (IAA) the viral cysteine protease p23 was converted to its active reduced form and subsequently alkylated. Furthermore, Greber et al. demonstrated that the protease which was alkylated/esterified in this way was inactive and as a consequence the proper disassembly of the capsids after entry of the target cells was hampered in a way that the viral DNA could not be translocated into the nucleus. Greber et al. showed that particle infectivity was reduced 20-fold by alkylating p23 as opposed to non-treated control particles. Furthermore, Greber et al. demonstrated a significant but unspecific alkylation of the cysteine-containing capsid proteins Hexon, Penton base and Fiber as well as of core protein pV with NEM after reduction by DTT. Furthermore, Jornvall and Philipson described a reactive cysteine residue in a solvent-accessible region of the Hexon capsid protein which could be alkylated by maleimide-based reagents (Jornvall, 1980).

BRIEF SUMMARY OF THE INVENTION

The objective of this invention is to provide a procedure by which viral vector particles can specifically be chemically modified in such a way that their natural capsid- and core protein-mediated biological functions are maintained; only the receptor-binding and/or membrane fusion functions may be altered. A further objective of this invention is to provide viral vector particles that were produced with this procedure.

The present invention refers to viral vector particles, comprising capsid proteins comprising an attachment site for the specific chemical modification of said vector particles, said attachment site comprising at least one genetically introduced cysteine residue which does not naturally exist in the capsid protein. The invention further relates to viral vector particles, further comprising a coupling partner coupled to said attachment site. Another aspect of the present invention is a viral vector particle, comprising a coupling partner coupled to an attachment site, said attachment site being a cysteine residue which naturally exists in a capsid protein. The viral vector particles may comprise one or more different coupling partners. One of said coupling partner may have one or more attachment sites.

The invention further refers to viral vector particles, whereby the coupling partner(s) is/are coupled onto said attachment site via disulfide, thioester, and/or thioether bonds. The coupling partner(s) may be cell-specific ligands, polymers, especially PEG-derivatives or HPMA-derivatives, nano gold particles, fluorescence dyes, magnetic substances, or biochemically/catalytically active substances.

The invention further refers to viral vector particles, whereby the attachment site has 1, 2, 3, 4, 5, 6 or more cysteine residues and whereby two or more cysteine residues directly follow each other or are separated by 1, 2, 3, or more amino acid residues which are different from cysteine. The attachment sites preferably comprise the amino acids according to SEQ ID NO:1, SEQ ID NO:2 or SEQ ID NO:3.

Viral vector particles of the present invention derive from gene transfer vectors based on including adenovirus, adeno-associated virus, retrovirus, lentivirus, or baculovirus. In case adenovirus is used as the viral vector particle the capsid proteins are selected from Fiber protein, Hexon, Penton base and protein IX. The Fiber protein preferably comprise the amino acids according to SEQ ID NO:13, SEQ ID NO:14 or SEQ ID NO:15.

Another aspect of the present invention refers to a nucleic acid molecule encoding a viral vector particle according to the present invention.

Another aspect of the present invention refers to a method for the generation of a viral vector particle according to the present invention, comprising the steps of: i) generation of a viral vector particle in packaging cell lines, comprising capsid proteins comprising an attachment site for the specific modification of the vector particles, said attachment site comprising at least one cysteine residue; ii) lysing of the packaging cells and subsequent purification of said viral vector particles in buffers with a pH from 5.0 to 9.0, preferably from 6.8 to 7.4, and more preferably at 7.3, the buffer saturated with atmospheric oxygen and optionally supplemented with reducing reagents, or in oxygen-reduced or oxygen-free buffers optionally supplemented with reducing reagents or in buffers optionally supplemented with reducing reagents in an atmosphere of Ar, He, N2 or CO2; iii) contacting of coupling partners with said viral vector particles and performing a coupling reaction under formation of a thioether, disulfide, or thioester bond in oxygen-saturated buffers with a pH from 5.0 to 9.0, preferably from 6.8 to 7.4, and more preferably at 7.3, the buffer optionally supplemented with reducing reagents, or in oxygen-reduced/oxygen-free buffers optionally supplemented with reducing reagents or in buffers optionally supplemented with reducing reagents in an atmosphere of Ar, He, N2 or CO2.

A further aspect of the present invention refers to the use of the viral vector particles according to the present invention as a therapeutic, prophylactic or diagnostic means in humans, primates and other vertebrates like cattle, pigs, birds, fish, or rodents.

DETAILED DESCRIPTION OF THE INVENTION

Figure 1:
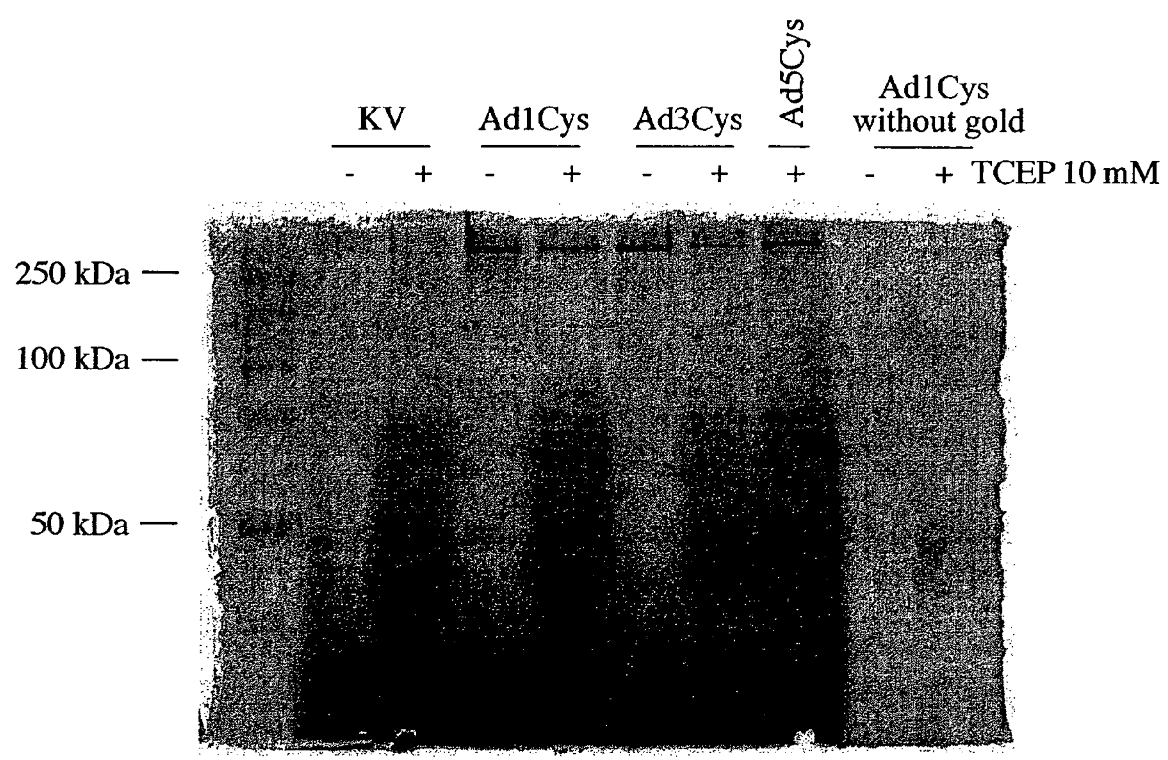
FIG. 1 depicts the alkylation results of the same number of Ad1Cys, Ad3Cys, Ad5Cys vector particles as well as genetically non-modified control vector with monomaleimide-nanogold particles and subsequent capsid protein separation by semi-native SDS-PAGE with gold-specific silver staining. (+) means pre-incubation with the reducing reagent TCEP (Tris (2-carboxyethyl)phosphine hydrochloride) (10 mM), (−) means no pre-incubation with reducing reagent. "KV" means genetically non-modified control vector particles incubated with monomaleimide nanogold, "Ad1Cys" means Ad1Cys-vector particles incubated with monomaleimide nanogold, "Ad3Cys" means Ad3Cys vector particles incubated with monomaleimide nanogold, "Ad5Cys" means Ad5Cys vector particles incubated with monomaleimide nanogold, "AdICys without Gold" means Ad1Cys vector particles not incubated with monomaleimide nanogold.

The term "vector particle" or "viral vector particle" or "virus vector particle" as used here refers to natural or artificial viral constructs for the uptake, multiplication, expression or transport of nucleic acids into cells. The term does not include any synthetically produced vector particles, i.e. particles produced without the help of cellular functions and processes going beyond the expression of capsid proteins. Examples for vector particles are viruses with a high degree of complexity such as adenoviruses, adeno-associated viruses, retroviruses, lentiviruses or baculoviruses. The vector particles are designed in such a way that they contain at least one therapeutic or analytical polynucleotide. This may be expressed and/or replicated. The vector particles can also include polynucleotide sequences that may have regulating features. Furthermore, the term vector particle can also include vector particles which are capable of lytic replication in other than production cells.

The term "therapeutic nucleic acid" refers to a polynucleotide sequence which upon delivery to a cell of an organism confers either therapeutic or prophylactic or diagnostic benefit.

The term "genetic modification" as used here refers to nucleic acid modifications of the polynucleotide sequences of natural capsid proteins of the viral vector particles resulting in a modified amino acid sequence of these proteins. These modifications are performed by standard molecular biology methods. Such a genetic modification may be passed on to the replicating genome upon vector particle replication and with this also to the replicating vector particles. Furthermore, the modified polynucleotide sequences may also be part of a production cell line being stably transfected with the modified polynucleotide sequence or part of a production plasmid that is not present in the purified vector preparation as used for the chemical modification.

The term "chemical modification" as used here refers to the modification of capsid proteins on structurally intact vector particles in the absence of production cells by chemical reactions and under formation of covalent chemical bonds. Such a chemical modification is not passed on to the replicating genome upon vector particle replication and with this also not to the replicated vector particles.

The term "tropism" as used here refers to the ability of the vector particles to infect/to transduce certain cells according to their surface composition.

The term "tropism modification" as used here refers to a procedure to alter the ability of vector particles to infect/to transduce certain cells according to their surface composition. In order to modify vector particle tropism, the particles are being given certain features such as certain affinities to receptors on the target cell's surface which they do not posses by nature. Furthermore, upon tropism modification naturally inherent features such as affinity for certain cellular receptors may be lowered or deleted, e.g. the affinity for CAR in case of Ad5.

The term "capsid protein" as used here refers to the group of proteins which is naturally involved in the formation of the vector particle capsid and is accessible by the solvent when the vector particle is in solution, e.g., Fiber or Hexon protein of Ad vector particles or VP2 of AAV vector particles. In case of enveloped viral vector particles it refers to protein components of the particle that are accessible by the surrounding solvent when the particle is in solution, e.g. the extra-membrane domains of the env proteins of retrovirus vector particles.

The term "coupling" as used here, refers to the thiol-specific chemical modification of thiol groups on the surface of the genetically modified vector particles under formation of covalent chemical bonds. As an example one can mention the formation of thio-ether bonds by the reaction of reduced thiol groups on the vector particle surface with maleimide goups. Furthermore, coupling refers to a procedure which maintains the structural integrity of the vector particles and their natural capsid and core protein functions. Only the receptor-binding and/or membrane fusion features may be altered.

The term "coupling partner" as used here, refers to molecules that are covalently and thiol-specifically attached to genetically modified vector particles (coupling). Functions of coupling partners may be the introduction of further or new reactive groups onto the vector particle surface, the introduction of new receptor specificities, or the shielding of vector particles, or the introduction of new catalytic or physical properties. Additionally, coupling partners are molecules which in the second or subsequent steps of the coupling process, attach to another coupling partner that has already attached to the vector particle surface.

The term "solvent-exposed domains" as used here refers to domains of the capsid proteins of structurally intact viral vector particles in solution that are in physical contact with the solvent. The physical contact with solvent may be generated by the application of reducing reagents or enzymatic treatment.

The term "oxidation number" as used here refers to a formal roman number describing the oxidation status of the sulfur atom of a cysteine residue and cysteine residue derivatives as obtained by chemical modifications and is calculated by the formula: 6-("number of electrons assigned to the sulfur atom of the cysteine residue/derivative")=oxidation number. The "number of electrons assigned to the sulfur atom of the cysteine residue/derivative" is determined based on the formal assumptions that 1) the sulfur atom and the 13-carbon atom of a cysteine residue/derivative have the same electronegativity and that 2) sulfur atoms have a higher electronegativity than hydrogen atoms. Therefore, the oxidation number of sulfur in a reduced thiol group of a cysteine residue as used here is -I and in a disulfide bond 0.

One aspect of this invention refers to viral vectors, comprising capsid proteins with an attachment site for the specific chemical modification of the vector particles, whereby the attachment site is a cysteine residue which does not naturally exist in the capsid protein. A further aspect refers to viral vector particles, comprising coupling partners attached to an attachement site, whereby the attachment site can be a naturally existing cysteine residue or a cysteine residue which was introduced into the capsid protein by recombinant DNA technology.

The vector particles can be produced by a combination of genetic and chemical procedures. Reactive thiol groups are introduced via cysteine residues into solvent-exposed capsid protein domains e.g. the Fiber Knob domain of Ad5 by genetic modifications. These genetic modifications permit the use of conventional production cell lines/systems and do usually not limit production yield. The genetically introduced thiol groups can optionally be kept in or transformed into a reactive i.e. reduced state by reducing reagents. The types and concentrations of the reducing reagents do not affect the integrity of the vector particles. The solvent-exposed reactive thiol groups obtained on the capsid proteins can be used for specific and covalent chemical coupling of any molecules such as ligands for tropism modification and/or polymers for shielding of the vector particles and/or marker molecules for labelling of vector particles and/or enzymes for certain catalytic activities of the vector particle surface. Either bio-irreversible covalent bonds (thioether, thioester) or bioreversible i.e. under the reducing conditions of the endosome or cytosol reversible covalent bonds (disulfides) can be formed between the coupling partner and the vector particle by choosing different chemical reagents for coupling. Furthermore, a combination of different coupling partners at different ratios and/or different chemical reagents may be used for coupling at the same time. Furthermore, coupling partners can introduce new attachment sites onto which coupling partners can be attached during further rounds of coupling.

A further aspect refers to the production of the viral vector particles according to the present invention, comprising the following steps: i) production of viral vector particle in production cell lines, comprising an attachment site for specific modification of said viral vector particle, whereby the attachment site consists of at least one cysteine residue, ii) cell lysis and/or vector particle purification in buffer solutions that are saturated with atmospheric oxygen and optionally supplemented with reducing reagents, or in oxygen-reduced/oxygen-free buffer systems that are optionally supplemented with reducing reagents, or in buffer systems saturated with Ar, He, N2 or CO2 that are optionally supplemented with reducing reagents, or combinations of the afore-mentioned buffer systems, iii) contacting the viral vector particles of step ii) with a coupling partner and performing a coupling reaction under formation of thioether, disulfide or thioester bonds in buffer solutions that are saturated with atmospheric oxygen and optionally supplemented with reducing reagents, or in oxygen-reduced/oxygen-free buffer systems that are optionally supplemented with reducing reagents, or in buffer systems saturated with Ar, He, N2 or CO2 that are optionally supplemented with reducing reagents, or combinations of the afore mentioned buffer systems with a pH in the range from 5.0 to 9.0, preferably from pH 6.8 to 7.4, and more preferably at 7.3. The isolated vector particles may be stored prior to further processing in the above listed buffers.

The basis of the described procedure is the genetic introduction of one or more reactive thiol groups into solvent-exposed domains of capsid proteins of viral vector particles via cysteine residues with suitable amino acids in their adjacency that permit control of the redox status of the cysteine residues as well as efficient alkylation/esterification. If more than one cysteine residue is being inserted, two or more cysteine residues may directly follow each other or may be separated by amino acids other than cysteines. Preferred are the sequence motives (i) LIGGGCGGGID ("1Cys") (SEQ ID NO:1), (ii) LIGCGCGCGID ("3Cys") (SEQ ID NO:2), (iii) LICCCCCID ("5Cys") (SEQ ID NO:3). The person skilled in the art can identify offhand that also motifs with differing numbers of cysteines (e.g., 2, 4, 6 or more ) and/or longer sequence motifs can be used. Furthermore it is evident that also motifs with interspersing and flanking amino acids other than glycine, serine, alanine, leucine, aspartic acid or combinations thereof may be used.

Furthermore, it is obvious that the procedure of genetic modification may also include cysteine-containing sequences with intrinsic receptor specificity or charges, e.g., sequences which are able to attach onto surface receptors of cells and/or facilitate the purification process of the vector particles.

The cysteine residues may for example be inserted into the solvent-exposed HI-loop of the Knob-domain of the capsid protein Fiber of adenovirus serotype 5. The person skilled in the art can identify offhand that alongside the solvent-exposed domains of the HI-loop in the Fiber protein also solvent-exposed areas in other regions of the Fiber protein as well as solvent-exposed regions in capsid proteins such as Hexon, Penton base and Protein IX are suitable for the insertion of the afore mentioned or similar motifs. Furthermore, it is obvious that not only adenovirus vectors may be used and in the used viruses potentially naturally existing and accessible cysteines can be modified with the invention-relevant procedure. As an example the VP1, VP2, and VP3 proteins of Adeno-associated virus (AAV) and its subtypes can be mentioned, as well as the env protein of retroviruses.

Additionally, the procedures apply to adenovirus vectors that are modified in such a manner that they no longer bear the natural Fiber protein but other trimerizing proteins for partial or complete substitution of the homotrimeric Fiber. Furthermore, the procedures apply to hybrid vectors which are composed of capsid proteins derived from different virus types, e.g. hybrid vectors composed of adenovirus and reovirus proteins. Furthermore, the procedure applies to chimeric vectors that have been composed of different Ad serotypes. Furthermore, the procedure applies to vectors which lack natural capsid components, e.g., Ad vectors that lack the fiber protein or parts of the fiber protein. In addition, the procedure applies to chimeric virus vectors other than adenovirus that are composed of different serotypes and to pseudotyped retro- and lentiviral vectors.

The cysteines may be incorporated into the vector particles by established procedures of recombinant DNA technology. For this purpose nucleic acid sequences encoding the cysteine sequence motifs are being incorporated into polynucleotide sequences which encode for the capsid protein of the vector particle to be modified. The thereby modified polynucleotide sequences are used for the production of the vector particles in production cell lines, e.g., N52E6 cells, 293 cells or PER.C6 cells, e.g., in case of Ad vector particles. The person skilled in the art is familiar with cell lines and production procedures that are used for production of adenoviral vectors and for production of other viral vectors such as for example vectors based on adeno-associated virus, retrovirus or lentivirus. In case of Ad vector particles, the nucleic acid is first of all transfected into the production cells (e.g., by the Ca-phosphate method). Subsequently, the production cell lines produce vector particles that can be harvested by cell lysis in a lysis buffer which usually is saturated with atmospheric oxygen such as phosphate-buffered saline (PBS) or in cell culture medium. Since the amounts of obtained vector particles are usually relatively low in this first step of production, the vector particles obtained by lysis are used again to infect production cell lines in order to obtain larger vector particle amounts. This is done by adding the vector particles obtained by lysis and optionally purified and/or concentrated to the production cells which are to be infected. This procedure is repeated with increasing production cell numbers up to 15 times (preferably 3-10 times). This process is called serial amplification. The buffers that are used to lyse the cells may contain reducing reagents such as tris-(2-carboxyethyl)-phosphine TCEP (1-10 mM), dithiothreitol DTT (1-10 mM), ascorbate (10-100 mM) or others. Additionally during serial amplifications right before the infection of production cells with vector particles antioxidative reagents such as ascorbate (50-100 mM) or vitamine E (1-100 mM) may be added to the cell culture medium in order to avoid the formation of vector particle aggregates prior to infection in the oxidative milieu of the cell culture medium.

Alternatively to the use of lysis buffers saturated with atmospheric oxygen optionally supplemented with reducing reagents during serial amplifications degassed buffer systems may be used, which may be obtained by vacuum, sonification, or a combination of both. Furthermore buffer systems may be used which were oxygen-depleted or oxygen-reduced by the application of argon, carbon dioxide, nitrogen or helium. Reducing reagents may also be added to the degassed buffers. Obviously all combinations of the mentioned procedures may be applied.

The buffer systems which are used for cell lysis may also be used for all purification and concentration procedures following the lysis of production cells at and after serial amplifications of the genetically capsid-modified vector particles. This also includes all purification and buffer exchange procedures prior to chemical modification of the vector particles (e.g., CsCl step gradient centrifugation, desalting by molecular sieves, dialysis). One must pay close attention to the application of materials and buffer systems which are free of divalent, metalic cations such as Mg2+ or Mn2+ in order to ensure stability and reactivity of the thiol groups to the vector particles. Chelating reagents such as EDTA or EGTA may be added to the buffers. All mentioned buffer systems are also used for vector particle storage as well as for purification and storage of the chemically modified or partially chemically modified vector particles.

By thiol-specific, chemical procedures various molecules (further on referred to as coupling partners) are attached to the vector particles by the formation of covalent chemical bonds (further on referred to as "coupling"). Here it is essential that the integrity of the vector particles as well as the natural capsid- and core protein-mediated vector particle functions are being maintained; only the natural receptor binding and/or membrane fusion functions may be altered. It is equally essential to maintain the structural integrity of the coupling partners.

The chemical modifications are carried out in buffer systems with a pH range from pH 5.0 to 9.0, preferably from pH 6.8 to 7.4, and more preferably 7.3. The chemical modifications can be carried out in a buffer solution saturated with atmospheric oxygen as well as with one or more of the previously mentioned buffer systems. The preferred buffer system is an oxygen- and metallic cation-free buffer containing 100 mM phosphate-buffered saline (PBS) solution. The person skilled in the art is familiar with the use of other inert buffer systems such as those based on HEPES. Furthermore, chemical reactions that are performed without changing the pH can also be performed in water. The used buffer system and the used reaction tube shall be free of divalent metallic cations such as Mg2+ or Mn2+ in order to ensure stability of the reduced thiol groups. Alternatively, chelators such as EDTA can be applied in order to stop undesirable interactions with thiol groups and divalent metal cations.

The coupling to genetically inserted thiols of the vector particles may take place through the formation of thioethers or thioesters (bio-irreversible covalent) or through formation of disulfide bonds (bioreversible). The formation of thioethers takes place with reagents such as maleimide derivatives, the formation of disulfide bonds either by reduced cysteines within the coupling partner or disulfide exchange reaction of cystin derivates or dithiopyridyl derivatives. The person skilled in the art is familiar with the reaction mechanisms and velocities. This knowledge permits variants of the coupling procedure according to the specific requirements of the coupling partners.

The coupling partners can be coupled directly to the vector particles by making use of intrinsic natural characteristics of the coupling partner. This can for example take place using naturally existing reduced thiol groups present in the coupling partner or by adding reducing reagents to the coupling partner to obtain reduced thiol goups e.g. from disulfide bridges present in the coupling partner. Furthermore, disulfide exchange reactions can be applied for direct coupling of the coupling partners.

Additionally, one may also apply genetically modified coupling partners such as recombinant proteins for thiol-specific coupling to vector particles, which received by genetic modification single cysteines or disulfide bridges for coupling via disulfide bonds or disulfide exchange reactions.

The coupling partners can also be coupled to the thiols on the surface of the vector particles after covalent chemical modification of the coupling partner. Here the coupling partners are chemically modified in such a way, that after this modification they posess covalently-coupled, thiol-specific reactive groups which in a subsequent step are applied for specific coupling onto the thiol groups of the vector particles. Thiol-specific reactive groups that can be inserted by chemical modification of coupling partner are for example maleimide groups for the formation of thioethers or dithiopyridyl groups for the formation of disulfide bridges or iodoacetyl derivatives for the formation of thioesters. These can be inserted by coupling reagents such as N-[E-maleimidecaproyloxy]succinimidester (EMCS) or Succinimidyl-6-[3-(2-pyridyldithio)-propionamido]hexanoat (SPDP) into the coupling partner. The person skilled in the art is familiar with the application of further reagents.

The chemical modification of the coupling partners for coupling onto the thiols on the vector particle surface can also be used to insert chemical groups that are not directly involved in the coupling process and which serve as spacers between coupling partners and vector particles. An example is the use of N-hydroxysuccinimid-polyethylenglykol-3400-maleimide (NHS-PEG3400-Mal). The use of spacers in the chemical modification of one or more coupling partners may serve to increase reaction efficiency by reduced steric hindrance as well as to increase the potency of the coupling partner by efficiently exposing its receptor-binding domains or to introduce further reactive groups for continued coupling. Obviously, apart from NHS-PEG-3400-Mal also other spacers can be used.

Clearly, one can also use coupling partners that themselves can bear specific reactive groups for the coupling of a second coupling partner in chronological order. Furthermore it is obvious that simultaneous coupling of several different coupling partners onto the vector particles can also occur.

The coupling partners for thiol-specific coupling onto the vector particles can fulfil different functions.

The first function consists in the mediation of new receptor specificities for retargeting of the vector particles which were modified in this manner. For this purpose proteins like transferrin can be applied whereby the characteristics of the coupling partners regarding receptor binding are transferred onto the vector particles by covalent coupling. It is obvious to the person skilled in the art that not only proteins with certain receptor specificities can be used here (e.g. transferrin, Epidermal Growth Factor EGF, basic Fibroblast Growth Factor bFGF), but also molecules of other substance categories. As an example mono- or polysaccharides such as galactose can be mentioned here which can mediate specific receptor binding. A further example for the application of coupling partners different from proteins are steroid hormones, which can also mediate receptor specificity. Furthermore, molecules with receptor binding characteristics that were designed with rational methods such as Molecular Modelling or derivatives of these and molecules that have been chemically synthesized or have been isolated from natural materials may be used for coupling. Also more complex molecules assembled of numerous subunits which may be covalently or even non-covalently linked e.g. viruses or virus vector particles may be used as coupling partners to be coupled to thiol groups on the vector particle surface. The vectors according to the present invention may also be coupled with coupling partners whereby developing a tropism for more than one cell type. Coupling of coupling partners to cysteine residues on the vector particle surface may also be performed before, at the same time, or after chemical modifications of the vector particle surfaceinvolving reactive groups different from thiols. For example before, at the same time, or after amino-PEGylation with amine-reactive electrophilically activated esters or before, at the same time, or after surface modification with amine-reactive HPMA thusly obtained vector particles might be subjected to thiol modification.

The second function consists in a steric shielding of the chemically modified vector particles by the coupling partners in order to avoid for example unwanted interactions with antibodies or the complement system or cellular components of the immune system. For this purpose derivatives of synthetic polymers such as polyethylene glycol (PEG) with different molecular weights and chain lengths can be applied. A further example for a synthetic polymer, whose derivatives are suitable for vector particle shielding and may thiol-specifically be coupled by one of the above described mechanisms onto the genetically modified vector particles is pHPMA (Fisher, 2001). Furthermore, molecules which confer new receptor specificities like proteins can themselves be used for shielding of vector particles.

The functions of mediating new receptor specificities by a coupling partner and shielding may be united by simultaneous or chronological coupling of two or more coupling partners onto the same vector particle, whereby tropism is created on the one hand and shielding is created on the other hand. Here it is obvious that both coupling partners can directly be coupled onto reactive thiol groups on the capsid surface or that one coupling partner offers reactive groups to the specific coupling of the second coupling partner onto the first. These reactive groups can for example be thiol, amino or carboxyl groups. Furthermore, it is obvious that a single coupling partner which combines both functions, the retargeting and the shielding, can also be used.

A third function of the coupling partners may be the labelling of the vector particles for example for analytic gene transfer with e.g. a fluorescence dye or nano gold particles as analytical markers.

A fourth function may be the possibility to alter the physical properties of the vector particles by for example coupling magnetic coupling partners to the vector particles and using the new physical properties like magnetism for, e.g., physical transduction methods or physical purification methods based on the physical properties conferred by the particular coupling partner.

A fifth function may be the possibility to alter the biochemical properties of the vector particles aside from receptor binding, i.e., to confer enzymatic activities to the vector particle by coupling enzymes or catalytically active fragments of enzymes like DNA recombinases or proteases onto the vector particles and transport these enzymatic or catalytic activities into target cells.

One prerequisite for the invention-relevant modification of vector particles is the availability of cysteine residues in solvent-accessible domains of the surface and/or the capsid proteins. Here it is irrelevant whether the viruses have an envelope or not. It is crucial that by reduction and/or alkylation/esterification of the thiol groups none of the biological vector functions are affected, only receptor-binding and/or membrane fusion features may be altered.

The invention-relevant modification of vector particles by specific coupling of ligands onto thiol groups which were genetically inserted into solvent-exposed domains, may be achieved for all viral vectors. The person skilled in the art is familiar with the existence of vectors that are based on a large number of different viruses. The viruses can be found in commonly accessible text books such as for example Fields, Virology. Especially interesting for gene therapy are currently vectors which are based on adenoviruses, adeno-associated viruses (AAV) or retroviruses and lentiviruses, and exist in different, with some viruses like AAV in many types and serotypes. For the invention-relevant modification it is required that thiol groups which are genetically inserted into solvent-exposed domains of capsid proteins and/or which are naturally available, are being kept in a reduced, reactive condition with mild reducing reagents and/or by the afore mentioned buffer systems or that they are being transferred into this condition.

The respective regions being suitable for the thiol specific coupling are positioned on the solvent-exposed domains of the viral capsid proteins so that the coupling of the coupling partners may be performed.

Example for further attachment sites for genetic insertion into certain loci of capsid proteins of the adenovirus type 5 are listed in the following table:

TABLE 1

| Protein | Locus | Insertion Site |
|---|---|---|
| Penton base | M22141, nt 435-2150 Protein-ID: AAA42519.1 | Substitution of the AA sequence: HAIRGDTFAT |
| pIX/ C-Terminus | AY339865, nt 3609-4031 protein ID: AAQ19288.1 | Attached onto the C-terminus of the AA-sequence: SSPPNAV |
| Hexon/ L1-Loop | AY339865, nt 18842-21700 protein ID: AAQ19298.1 | Substitution of the wt-AA-sequence: TTEAAAGNGDNLT |

The modified viral vector particles according to the present invention can especially be applied for therapeutic purposes for gene therapy or vaccination or for functional and diagnostic analysis in vivo in humans, primates, or other vertebrates like cattle, pigs, birds, fish or rodents or in vitro in tissue or cell cultures comprising cells from vertebrates, in particular from humans and primates like cattle, pigs, birds, fish or rodents. Disorders can be inherited disorders which are for example caused by a mutation in one gene. Furthermore, the modified viral vector particles according to the present invention can be used for the treatment of acquired disorders such as for example tumor diseases or disorders of the central nervous system such as Parkinson syndrome. In these situations, i.e. in genetic disorders or in acquired disorders, modified viral vector particles according to the invention and carrying one or more therapeutic nucleic acids are used to enable improved and/or selective transduction of cells in vitro and in vivo, in order to allow expression of one or more therapeutic nucleic acids in these cells. The person skilled in the art is familiar with the use of viral vectors for the treatment of genetic or acquired disorders and textbooks and publications can be consulted for the selection of specific nucleic acids for the treatment of genetic or acquired disorders. The person skilled in the art is also familiar with ways to administer modified viral vector particles to individuals/animals, such as for example by systemic administration (intravenously, intraarterially), by administration through body orifices or by local needle or katheter injection into a tissue or organ. Additionally, the invention-relevant modified viral vector particles can also be applied as vaccines for example for prophylactic vaccination against HIV or other infectious diseases or as tumor vaccine. In fact, the use of modified viral particles for prophylactic or therapeutic vaccination against infections or neoplastic disorders is a preferred application. It is well known to the scientific community that the use of viral vectors for vaccination is frequently impaired or even prevented by pre-existing either B-cell or T-cell-mediated immunity that is directed to the particular vector that is used to deliver the particular gene. Also, even if in an individual there are no pre-existing antibodies to the viral vector that is used for vaccination, upon a first application of the vector usually a strong immune response is raised, preventing a second administration of the same viral vector.

The present invention enables strategies to circumvent these problems by thiol-specific coupling of either shielding reagents such as polyethylene glycol or targeting ligands, or both, to the surface of the viral vector particle, thereby preventing the recognition of viral vector surface structures by the immune system and at the same time targeting the vector to the cells and/or organs of interest.

The transgenes that may be expressed by the vector particle genome are not critical for the invention. Here it may concern for example muscle proteins, clotting factors, membrane proteins or cell cycle-regulating proteins. Example for a muscle protein is dystrophin, an example for a secreted protein is the clotting factor VIII, an example for a membrane protein is the cystic fibrosis transmembrane regulator protein (CFTR). Furthermore it may concern genes that originate from pathogens such as for example the AIDS virus HIV or animal viruses or parasites and are being expressed by the viral vector particle as a vaccine.

The use of the invention-relevant modified viral vector particles may occur in vitro or in vivo. In vitro gene transfer occurs outside of the body for example by adding vector particles to tissue or cell culture cells. In in vivo gene transfer vector particles are being applied in different ways, depending on the tissue that is to be transduced. Examples for the ways in which vector particles can be applied are injection into the arterial or venous vessel system, direct injection into the appropriate tissue (for example lung, liver, brain, muscle), instillation into the appropriate organ (for example lung or gastrointestinal tract) or direct application onto a surface (for example skin or bladder). The vector particles used for this purpose are chemically modified with, e.g., the ligand or shielding polymer by thiol-specific coupling of the ligand to the vector particle surface, in such a way that allows for ligand-specific interaction with its target receptor and subsequent particle uptake.

The basis of this procedure is the invention-relevant combination of genetic and chemical modifications of a solvent-exposed domain of a capsid protein of viral vectors whereby the chemical modification occurs through formation of covalent and optionally bioreversible bonds. A central aspect of the procedure is to maintain the integrity and the natural and capsid and core protein-mediated biological functions of the modified vector particles; only the receptor binding characteristics/membrane fusion characteristics may be altered. The basic advantages are summerized as follows: (i) vector particle production for the chemical capsid modification with conventional procedures through high yields (ii) high flexibility with the use of coupling partners, particle shielding, labelling or giving new physical or biochemical/catalytical characteristics (iii) high specificity of the chemical capsid modifications with optional bioreversibility.

Advantageous is also (1) the selective genetic insertion of reactive thiol groups onto the capsid surface before the chemical modification of the vector particles, (2) the potential use of sequences for genetic modification of the vector capsids without known receptor binding characteristics, (3) the post-productional, covalent and optionally bioreversible chemical modifications of at least one part of the genetically introduced cysteines, (4) the possibility for covalent and thus stable coupling, (5) the use of sequences for the genetic modifications as a basis for chemical modification for which no natural function is described, (6) the use of procedures that may specifically and solely use the genetically introduced reactive thiol groups without covalently modifying any wild-type existing amino acids, (7) the use of procedures that specifically modify the oxidative status of the vector particles, (8) the avoidance of crosslinking within the capsid through the high specificity of the used chemical reactions, (9) the possibility for the formation of bioreversible, i.e. in the reducing milieu of the endosome or cytosol reversible (disulfide) bonds, (10) the use of small reactive groups (e.g. maleinimides) for the chemical modification of the vector particles by the formation of covalent bonds, (11) the possibility for the use of non-peptide/non-protein coupling partners, (12) the possibility of shielding of the vector particles through the choice of appropriate coupling partners.

It is essential for the invention that with the present procedure for the modification of vector particles for gene transfer the natural capsid- and core protein-mediated biological functions of the vector particles are entirely maintained; only the receptor binding and/or membrane fusion characteristics may be altered.

The possibility of using thiol groups of cysteine residues that were genetically introduced into the vector particle for the chemical modification of the vector particles by changing their oxidative status and maintaining their integrity and function was unexpected and surprising for the following reasons: the invention-relevant procedures allow for the application of reducing reagents with subsequent alkylation of the reduced thiol groups for the specific chemical modification of the solvent-exposed cysteine residues of the genetically modified vector particles. Surprisingly the inventors of the present application could not observe alkylation of the viral cysteine protease p23 of Ad5 neither for vector particles with cysteine residues that were genetically introduced into the capsid proteins nor with genetically unmodified vector particles after chemical reduction and alkylation with monomaleimide nanogold particles. Furthermore, no change of infectivity was detected for particles that had been reduced and subsequently treated with alkylating reagents as compared to untreated control particles. According to the present standard of knowledge one would have expected that after applying reducing reagents and alkylating reagents not only the solvent-exposed thiols which were genetically inserted, but additionally also naturally existing thiols present in the capsid proteins Hexon, Penton base and Fiber as well as core protein pV would have been alkylated. Surprisingly the inventors discovered that after reduction of adenoviral vector particles without genetic modification none of these proteins was alkylated by monomaleimide nanogold particles. However, genetically introduced, solvent-exposed cysteine residues could be alkylated with the same procedure efficiently and highly specific. The selective and specific alkylation of genetically inserted cysteine residues is one of the central tasks of the procedure described here.

The following examples explain the invention and should not be regarded as restricting. If not otherwise mentioned, standard methods of molecular biology were used, such as described by Sambrook et al., 1989, Molecular cloning: A Laboratory Manual $2^{nd}$ Edition, Cold Spring Harbor Laboratory Press, Cold Spring Harbor, N.Y.

1. Production of plasmids pAd1Cys, pAd3Cys, pAd5Cys

The plasmids pAd1Cys, pAd3Cys, pAd5Cys are infectious first generation vector plasmids which encode E1-deleted, EGFP-expressing adenovirus vector particles. Their production is carried out in serveral steps which are described as follows.

a) Production of pFKG pFKG is based on pEGFP-N1 (Clontech) and contains an expression cassette for the EGFP gene under control of the human CMV promoter. For the subsequent cloning steps it was necessary to delete a BstBI restriction site from the expression cassette under formation of the plasmid pFKG. For this 10 μg pEGFP-N1 (Clontech) were digested 3 h at 37° C. with 100 U of the restriction endonuclease SalI in a total volume of 100 μl restriction buffer A (150 mM NaCl, 10 mM Tris-HCl, 10 mM $MgCl_2$, 1 mM Dithiothreitol, pH 7,9). The DNA from the digestion was precipitated with ethanol, washed for 5 min at room temperature with 70% ethanol and resuspended in 95 μl restriction buffer B (50 mM NaCl, 10 mM Tris-HCl, 10 mM $MgCl_2$, 1 mM Dithiothreitol, pH 7,9). 100 U of the restriction endonuclease XhoI in a volume of 5 μl were pipetted to the solution and incubated at 37° C. for 3 h. That was followed by an extraction of the solution with phenol/chloroform, an ethanol precipitation and the DNA was resuspended in 50 μl Tris-HCl (10 mM Tris, pH 7,5). 100 ng of the DNA were dissolved with 400 U T4-DNA ligase in a total volume of 10 μl in ligation buffer (50 mM Tris-HCl, 10 mM $MgCl_2$, 10 mM Dithiothreitol, 1 mM ATP, 25 μg/ml bovine serum albumin) and incubated for 12 h at room temperature. Transformation-competent XL2-blue *Escherichia coli* (Stratagene) were transformed with 1 μl of this solution and incubated for 14 h on agar plates at 37° C. The preparation of the DNA from the clones was carried out with standard methods (Sambrook et al., 1989, Molecular cloning: A Laboratory Manual $2^{nd}$ Edition, Cold Spring Harbor Laboratory Press, Cold Spring Harbor, N.Y.).

b) Production of pGS109 pGS109 is an infectious first generation Ad vector plamid which encodes E1-deleted adenovirus particles and bears the expression cassette for EGFP from pFKG. For the cloning of the expression cassette for EGFP from pFKG the unique PacI-site in pGS66 (Schiedner, 2000) was used. For this 10 μg pGS66 were digested with 100 U of the restriction endonuclease PacI in 100 μl total volume in restriction buffer C for 3 h at 37° C. (10 mM Bis-Tris-Propan-HCl, 10 mM $MgCl_2$, 1 mM Dithiothreitol, pH 7,9). The solution was extracted with phenol/chloroform, the DNA was precipitated with ethanol and resuspended in 95 μl polymerase buffer (50 mM NaCl, 10 mM Tris-HCl, 10 mM $MgCl_2$, 1 mM Dithiothreitol, 50 μM dATP, 50 μM dTTP, 50 μM dCTP, 50 μM dGTP, pH 7,9). 15 U T4-DNA-polymerase were added to the solution in a total volume of 5 μl and the solution was incubated for 15 min at 12° C. Subsequently a phenol/chloroform-extraction and an ethanol precipitation were carried out. The DNA was washed with 70% ethanol and resuspended in 99 μl restriction buffer C. 10 U CIP were added and incubated for 1 h at 37° C. Subsequently a phenol/chloroform extraction and an ethanol precipitation were carried out. The DNA was washed with 70% ethanol and resuspended in 40 μl Tris-HCl pH 7,9. This DNA was afterwards called pGS66-Pac. In order to clone the expression cassette for EGFP from pFKG into the blunt-ended PacI-site, 10 μg pFKG in a total volume of 100 μl restriction buffer D (100 mM NaCl, 50 mM Tris-HCl, 10 mM $MgCl_2$, 1 mM Dithiothreitol, pH 7,9) were digested with 50 U AflIII for 5 h at 37° C. and subsequently precipitated with ethanol and resuspended in 95 μl restriction buffer B. 100 U of AflII were added to the DNA (total volume of the reaction: 100 μl) and digested for 3 h at 37° C. dATP, dTTP, dCTP, dGTP were added to final concentrations of 33 μM each and 10 U DNA-polymerase I (Klenow-Fragment) were added. The solution was incubated for 20 min at 30° C. and the resulting DNA fragments were separated by gel electrophoresis (1% agarose gel). The AflII/III-fragment containing the expression cassette for EGFP (length 1697 bp) was cut out from the gel and purified by the Qiagen Gel Extraction Kit (Qiagen, Hilden), ethanol-precipitated and resuspended in 40 μl Tris-HCl pH 7,5. For the ligation of this fragment into the blunt-ended PacI-site of pGS66 25 ng of the fragments were dissolved with 100 ng pGS66-Pac in a total volume of 10 μl ligation buffer with 400 U T4-DNA-Ligase and incubated for 12 h at room temparature under formation of pGS109. Transformation-competent XL2-blue *Escherichia coli* (Stratagene) were transformed with 1 μl of this solution and incubated for 14 h on Agar plates at 37° C. The preparation of DNA from the clones was carried out with standard methods. Only DNA from one clone was used in the subsequent steps whereby the transcriptional orientation of the EGFP expression cassette in the subsequently used clone was parallel to the Major-Late-Promoter of the adenovirus genome.

c) Production of pGS110 pGS110 is an infectious first generation plasmid which encodes infectious adenovirus particles, bears the expression cassette for EGFP from pFKG and allows the insertion of oligonucleotide sequences into the Fiber gene. The Fiber gene has after nt 32665 of Wildtype-Adenovirus (Locus AY339865, gi:33465857) an insertion with the sequence TTAATTAAGACTAGTACAATCGAT, which allowed a simple cloning of additional insertions via a PacI- and a ClaI-restriction site. For the production 10 μg pGS109 with 50 U BstBI in a total volume of 100 μl restriction buffer E (50 mM K-Acetat, 20 mM Tris-Acetat, 10 mM Mg-Acetat, 1 mM Dithiothreitol, pH 7,9) were digested for 2 h at 65° C. After cooling down to 37° C. 50 U PmeI were added and digested for 4 h at 37° C. The fragments were separated in a 0,8% agarose gel and the 10 kB-fragment, which contains the EGFP-expression cassette from pFKG was isolated from the gel by the Qiagen Gel Extraction Kit (Qiagen, Hilden), precipitated with ethanol and resuspended in 40 μl Tris-HCl pH 7,5. This fragment was afterwards called Ad-left-EGFP. 10 μg pVB4 (Biermann, 2001) with 50 U BstBI in a total volume of 100 μl restriction buffer E were digested for 2 h at 65° C. After cooling down to 37° C. 50 U PmeI was added and digested for 4 h at 37° C. 10 U CIP were added and incubated for 1 h at 37° C. The fragments were separated in a 0,8% Agarose gel and the 25 kb-fragment was isolated from the gel via electroelution, precipitated with ethanol, and resuspended in 40 μl Tris-HCl pH 7,5. This fragment was afterwards called Ad-right-Fiberinsertion. 100 ng of the fragement Ad-right-Fiber-insertion and 120 ng of the fragment Ad-left-EGFP were dissolved in a total volume of 10 μl ligase buffer with 400 U T4-DNA-Ligase and ligated for 12 h at room temperature under formation of pGS110. XL2-blue *Escherichia coli* (Stratagene) were transformed with 1 μl of this solution and incubated for 14 h on agar plates at 37° C. The preparation of DNA from the clones was carried out with standard methods.

d) Production of pAd1Cys

For the production of pAd1Cys, an infectious first generation vector plasmid which encodes E1-deleted adenovirus vector particles, that bear an expression cassette for EGFP and which carries the oligonucleotid sequence 5'-TTAATTGGCGGCGGATGCGGTGGCGGCATCGAT-3' (SEQ ID NO:4), which encodes the amino acid sequence LIGGGCGGGID inserted after amino acid (aa) 543 of Wildtype-Adenovirus-Fiber (AAQ19310.1)), 10 μg of pGS 110 were digested in a total volume of 100 μl restriction buffer C with 100 U PacI for 2 h. The DNA was precipitated with ethanol and was resuspended in 90 μl restriction buffer E. 50 U ClaI in a volume of 10 μl were added and the mixture was incubated for 3 h at 37° C. 10 U CIP were added, incubated for 1 h at 37° C., the DNA was subjected to a phenol/chloroform-extraction, precipitated with ethanol, washed with 70% ethanol and resuspnded in 40 μl Tris-HCl pH 7,5. This DNA was afterwards called GS110-CIP. 1 μg of the synthetically produced 5'-phosphorylated oligodesoxyribonucleotides 1Cys-seq (5'-TGGCGGCGGATGCGGTGGCGGCAT-3') (SEQ ID NO:7) as well as 1Cys-rev (5'-CGATGCCGCCACCGCATCCGCCGCCAAT-3')(SEQ ID NO:8) was boiled in 40 μl Tris-HCl 10 mM, 1 mM EDTA for 5 min in a water bath and slowly cooled down to room temperature. The thereby formed double-stranded DNA was afterwards called Oligo1Cys. 100 ng GS110-CIP were ligated in a total of 10 μl Ligation buffer with 1 ng Oligo1Cys and 400 U T4 DNA-Ligase under formation of pAd1Cys. Competent XL2-blue *Escherichia coli* (Stratagene) were transformed with 1 μl of this solution and incubated for 14 h on agar plates at 37° C. The preparation of DNA from the clones was carried out with standard methods.

e) Production of pAd3Cys

The production of pAd3Cys, an infectious first generation vector plasmid which encodes for E1-deleted adenovirus vector particles, which bear an expression cassette for EGFP and the oligonucleotide sequence 5'-TTAATTGGCTGCGGATGCGGTTGCGGCATCGAT-3' (SEQ ID NO:5) which encodes for the amino acid sequence LIGCGCGCGID (inserted after aa 543 of wildtype adenovirus Fiber (AAQ19310.1)), correponds in its procedures with the production of pAdICys, but the 5'-phosphorylated oligodesoxyribonucleotides 3Cys-seq (5'-TGGCTGCGGATGCGGTTGCGGCAT-3')(SEQ ID NO:9) and 3Cys-rev (5'-CGATGCCGCAACCGCATCCGCAGCCAAT-3') (SEQ ID NO:10) were used instead of 1-seq and 1Cys-rev.

f) Production of pAd5Cys

The production of pAd5Cys, an infectious first generation vector plasmid which encodes for E1-deleted adenovirus vector particles, which bear an expression cassette for EGFP and the oligonucleotide sequence 5'-TTAATTTGCTGTTGTTGCTGCATCGAT-3' (SEQ ID NO:6), which encodes for the amino acid sequence LICCCCCID (inserted after aa 543 of wildtype adenovirus Fiber (AAQ19310.1)), corresponds in its procedure with the production of pAdICys, but the 5'-phosphorylated oligodesoxyribonucleotides 5Cys-seq (5'-TTGCTGTTGTTGCTGCAT-3') (SEQ ID NO:11) und 5Cys-rev (5'-CGATGCAGCAACAACAGCAAAT-3') (SEQ ID NO:12) were used instead of 1Cys-seq and 1Cys-rev.

2. Production of Vector Particles

For the production of the vector particles the plasmids pAd1Cys, pAd3Cys and pAd5Cys were linearized with SwaI and 4-6 μg of the linearized plasmids were transfected via standard transfection methods into 1-2E+06 N52E6-cells. These plasmids are infectious adenovirus-shuttle-plasmids for the production of E1-deleted first generation vector particles, which replicate in adenovirus E1-transcomplementing cell lines such as N52E6 and may produce vector particles. The person skilled in the art is familiar with the methods for the production of the corresponding Ad vector particles. It should be mentioned that the buffers used for cell lysis were invariably saturated with atmospheric oxygen. The purification of the vector particles was carried out by one CsCl density step gradient followed by two continuous CsCl density gradients.

Upon observation of macroscopical aggregates in the CsCl step gradient with Ad5Cys these aggregates were taken off the gradient, treated for 1 h with 10 mM DTT or 10 mM TCEP or 50 mM ascorbate and the same concentrations of the same reducing reagent were added to the subsequent continuous CsCl density gradient. Alternatively, for Ad5Cys, the buffer in which the cells were lysed prior to the loading of the CsCl step gradient, was also supplemented with the afore mentioned reducing reagents. The person skilled in the art is familiar with the techniques of the CsCl step and continuous density gradient centrifugation. The desalting of the vector particles after the second continuous CsCl step gradient was carried out with molecular sieves based on Sephadex G-25. The person skilled in the art is familiar with these desalting techniques.

The vector particles were stored in TBS or PBS plus 10% glycerol at −80° C. For Ad5Cys the reducing reagents 10 mM TCEP or 10 mM DTT or 50 mM ascorbate were added. The yields of the vector particles were determined after purification and desalting with standard methods that the person skilled in the art is familiar with (measuring of the optical density after particle lysis, measuring of the protein content, measuring of the infectious units with a DNA-based assay, measuring the total number of particles with DNA-based assay). Here it could be noticed that in comparison to non-modified first generation vector particles, the genetic insertion of cysteine residues on the capsid surface had no negative effects regarding the yields. The inverse bioactivities of the vector particle preparations did not show significant differences compared to the non-capsid-modified vector particle preparations.

3. Measuring of the Aggregates

The identification of spontaneous aggregate formation in buffers that were saturated with atmospheric oxygen was carried out with photon correlation spectroscopy PCS. The polydispersity index (PI) of the individual assays was taken as a measure for the existence of particles with widely differing sizes and therefore for the existence of particle aggregation. The person skilled in the art is familiar with this method. It could thus be shown that the vector particles AdICys and Ad3Cys spontaneously form small, but soluble aggregates (PI: 0,5-1,0, unmodified control vector: 0,05), which surprisingly do not interfere with the purification and the capsid- and coreprotein-mediated biological functions of the vector particle including receptor binding. Furthermore it could also be shown that by adding reducing reagents the formation of aggregates is reversible. The controllable and reversible formation of particle aggregates serves as an example for the bioreversible, i.e., the under the reducing conditions of the endosome/cytosol reversible coupling of molecules via disulfide bridges.

4. Measuring of the Capsid- and Coreprotein-Mediated Biological Functions of Modified, Oxidized and Reduced Vector Particles.

The biological function of the vector particles in the sense of an efficient gene transfer was verified in transduction experiments with A549 cells and flow cytometry-based analysis of transgene expression (EGFP). Here it could be shown that both with and without application of reducing reagents the capsid- and coreprotein-mediated biological functions of the vector particles were not inhibited. After reduction with different reducing reagents (10 mM TCEP, 10 mM DTT, 50 mM ascorbate) the modified vector particles were able to transduce the mentioned cell line with the same efficiency as untreated modified and non-modified control vector particles.

5. Gold-Labelling

To thiol-specifically and maleimide-mediated alkylate the genetically modified vector particles the same number of particles of the different vector particle preparations (Ad1Cys, Ad3Cys, Ad5Cys, non-modified control vector particles) was incubated with a 100 fold molar excess of mono-maleimide nanogold particles (Molecular Probes) for 24h at 4° C. with and without addition of 10 mM TCEP. The reaction was stopped by the addition of 1 μmol cysteine. The analysis of the coupling was carried out by semi-native SDS-PAGE with subsequent gold-specific silver staining. Here it was unexpected and very surprising to note that gold coupling occured only to the genetically modified Fiber proteins and not to the viral protease p23, the core Protein V or the capsid proteins Hexon or Penton base. This specific coupling corresponds to the bands at 270 kDa. This size is put together from Fiber trimers (approx. 200 kDa) plus three gold particles per Fiber trimer (together approx. 70 kDa). After vector particle purification, specificity could surprisingly also be shown for the region of the small molecular weights. Furthermore it was surprising to note that even without the application of reducing reagents the vector particle preparations Ad1Cys and Ad3Cys showed solvent-exposed reduced thiol groups which were accessible to an efficient alkylation (up to three gold particles per Fiber trimer).

6. Transferrin-Coupling onto Non-Reduced Vector Particles Ad1Cys as an Example for a Specific Alkylation with Retargeting Effect To specifically modify the genetically introduced thiol groups on the vector particle surface of Ad1Cys by a maleimide-mediated alkylation with transferrin derivatives 1 mg of apo-transferrin was incubated with 0,021 mg N-hydroxysuccinimid-polyethylen-glycol-3400-maleimid in a total volume of 200 μl of degassed and subsequently argon-saturated PBS for 4 h at room temperature. One μl of this reaction was added to $10^{11}$ vector particles Ad1Cys in a volume of 80 μl PBS/10% glycerol. This alkylation reaction was incubated in an argon atmosphere for 20 h at room temperature. After alkylation the modified vector particle preparation was used to transduce 5E+05 K562-cells with increasing particle numbers of 100, 1000, and 5000 particles per cells. Immediately before transduction 3 μl of 1 mM Fe(III)-citrate-solution were added per 350 μl cell culture medium, in order to reconstitute the transferrin which had coupled onto the vector particles. The same particle numbers of non-alkylated vector particle and non-alkylated particles mixed with free transferrin as controls were used as well as the same particle numbers of a non-capsid-modified vector. The number of EGFP-expressing cells was determined by flow cytometry 30 h after transduction. Table 2 gives an overview over the percentage of EGFP-positive cells in the individual experiments. The means of 4 independent experiments are listed. The data show that the authors surprisingly succeeded in alkylating free cysteines on the vector particle surface by maleimide-modified transferrin even without reduction and even after identifying small vector particle aggregates by photon-correlated spectroscopy. Furthermore, by this specific alkylation reaction the receptor binding characteristics of the particles were successfully altered. This was not obvious from published data.

TABLE 2

| Vector particles | 100 Particles/Cell | 1000 Particles/Cell | 5000 Particles/Cell |
|---|---|---|---|
| Free non-modified control vector particles without Tf | 11.87% | 45.49% | 79.65% |
| free Ad1Cys without Tf | 9.17% | 47.42% | 83.02% |
| free Ad1Cys with free Tf | 9.30% | 47.47% | 83.51% |
| Ad1Cys with maleimide -coupled Tf | 46.73% | 90.49% | 94.42% |

7. Example for an Alkylation after Reduction: Transferrin-Coupling to Reduced Ad5Cys Vector Particles does not Interfere with Vector Particle Infectivity The same procedure as described above was used to transferrin-alkylate 1E+010 Ad5Cys vector particles that had been reduced by 10 mM TCEP. K562-were transduced and 36 h after transduction cells were analyzed by flow cytometry. Table 3 shows the results (means of 2 independent experiments). This surprisingly shows that after reduction and alkylation no loss in vector particle infectivity occurs. This correlates well with the results form the gold-labeling experiments that did not show alkylation of the viral protease. A significant targeting effect cannot be observed in this experiment because under reducing conditions transferrin was reduced and unable to bind iron and therefore lost its ability to bind to the transferrin receptor.

TABLE 3

| Vector particle | 100 Particles/Cell | 1000 Particles/cell | 5000 Particles/cell |
|---|---|---|---|
| reduced Ad5Cys, without Tf | 3.88% | 32.29% | 63.91% |
| Reduced Ad5Cys, with free Tf | 5.78% | 42.75% | 75.33% |

8. Example for Specific Chemical Modification of Genetically Introduced Thiol Groups after Chemical Modification of the Vector Particle Surface by PEGylation with an Amine-Reactive, Electrophilically Activated PEG-Derivative.

Figure 2:
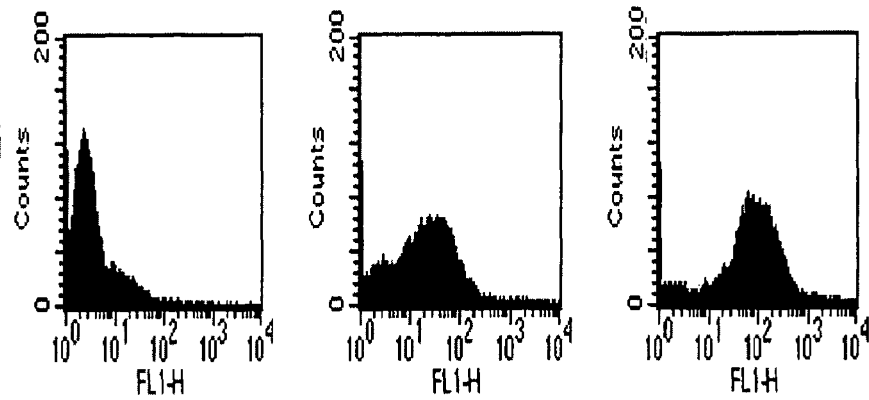
FIG. 2 demonstrates successful chemical modification of the genetically introduced thiol groups in the vector Ad1Cys after shielding by amino-PEGylation of the vector particles. Shown are typical results from flow cytometry to analyze EGFP expression in K562 cells. "pMOI" means particle MOI (number of physical vector particles used to transduce K562 cells). "AdICys unmodified" is the chemically unmodified Ad1Cys vector. "Ad1Cys+SPA-PEG" means amino-PEGylated Ad1Cys vector. "Ad1Cys+SPA-PEG+Tf-Mal" means amino-PEGylated Ad1Cys vector which, after amine modification, was thiol-specifically modified with maleimide-transferrin (Tf-Mal).
Figure 2:
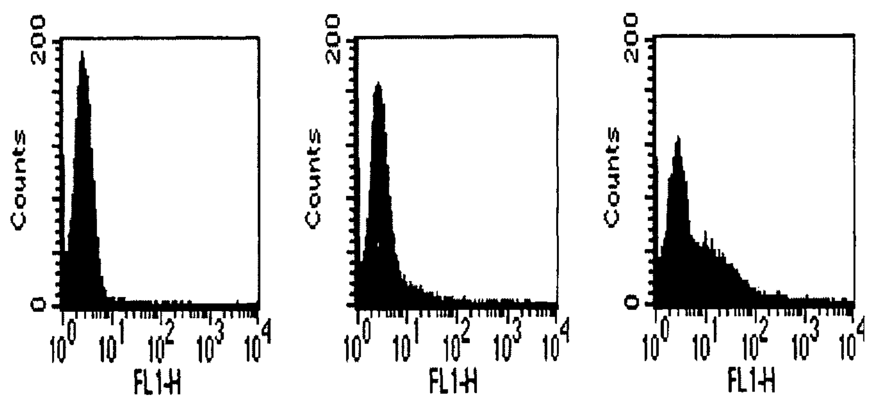
Figure 2:
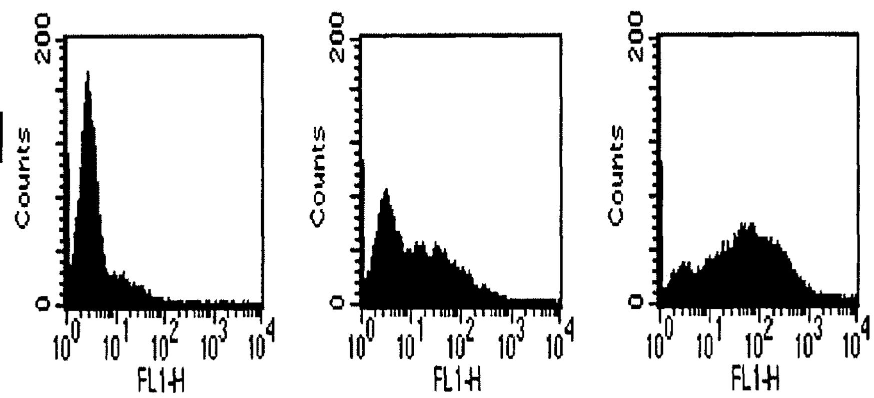

For amino-PEGylation, mPEG2000-SPA (Nektar Therapeutics) was used. To 5E+010 physical particles of Ad1Cys in a total volume of 100 μl of argon-bubbled 50 mM HEPES buffer, pH 7.3, 0.3 mg of mPEG2000-SPA was added and reacted under argon for 3 h at room temperature. The reaction was quenched by the addition of a 1.5-fold excess of free lysine over reactive mPEG-SPA molecules and incubation at room temperature for 2 h in an argon atmosphere. Finally, to attach transferrin to the thiols of the PEGylated vector particles, NHS-PEG3400-Mal-modified transferrin was added in a 5-fold molar excess over cysteine residues and reacted overnight under argon (see example 6). After overnight reaction particles were used to transduce K562 cells in the same way as described in Example 6 and 24 h later the number of EGFP expressing cells was determined by flow cytometry. FIG. 2 shows a typical result for a chemically unmodified vector ("Ad1Cys"), an amino-PEGylated vector without thiol-specific modification ("Ad1Cys+SPA-PEG"), and an amino-PEGylated and subsequently thiol-modified vector carrying transferrin covalently attached to the genetically introduced thiol groups ("Ad1Cys+SPA-PEG+Tf-Mal"). The amino-PEGylated vector showed significantly reduced transduction efficiency compared to the unmodified vector Ad1Cys. Surprisingly, after further modification of the amino-PEGylated vector with thiol-reactive maleimide-transferrin (see example 6) the vector particles showed significantly increased transduction efficiency on K562 cells. This demonstrates that 1) after amino-PEGylation with an amine-reactive PEG the genetically introduced thiol groups on the vector particle surface remain accessible for chemical coupling and 2) that this can be used to retarget such thiol-bearing PEGylated vector particles to the transferrin receptor pathway by chemical coupling of transferrin to the vector particle surface. It was unexpected and very surprising that the thiol groups remained accessible for chemical modification with large coupling partners like transferrin after modification of the vector particle surface with a shielding reagent like mPEG-SPA2000.

REFERENCES

The following references, to the extent that they provide exemplary procedural or other details supplementary to those set forth herein, are specifically incorporated herein by reference:

Biermann V, Volpers C, Hussmann S, Stock A, Kewes H, Schiedner G, Herrmann A, Kochanek S. Targeting of high-capacity adenoviral vectors. Hum Gene Ther. 12:1757-69 (2001).

Dmitriev I, Krasnykh V, Miller CR, Wang M, Kashentseva E, Mikheeva G, Belousova N, Curiel DT. An adenovirus vector with genetically modified Fibers demonstrates expanded tropsim via utilization of a coxsackievirus and adenovirus receptor-independent cell entry mechanism. J. Virol. 72:9706-13 (1998).

Fields et al., Fields Virology, 3$^{rd}$ edition, Lippincott-Raven Publishers Philadelphia, Philadelphia (1996).

Fisher KD, Stallwood Y, Green NK, Ulbrich K, Mautner V, Seymour LW. Polymer-coated adenovirus permits efficient retargeting and evades neutralising antibodies. Gene Ther. 8:341-8 (2001).

Greber UF, Webster P, Weber J, Helenius A. The role of adnocirus protease on virus entry into cells. EMBO J. 15:1766-77 (1996).

Jörmvall H, Philipson L. Limited proteolysis and a reactive cysteine residue define accessible regions in the native conformation of the adenovirus hexon protein. Eur J. Biochem. 104:237-47 (1980).

Schiedner G, Hertel S, Kochanek S. Efficient transformation of primary human amniocytes by E1 functions of Ad5: generation of new cell lines for adenoviral vector production. Hum Gene Ther. 11:2105-16 (2000).

Stubenrauch K, Gleiter S, Brinkmann U, Rudolph R, Lilie H. Conjugation of an antibody Fv fragment to a virus coat protein: cell-specific targeting of recombinant polyomavirus-like particles. Biochem J. 356:867-73 (2001).

Wang Q, Lin T, Johnson JE, Finn MG. Natural supramolecular building blocks. Cysteine-added mutants of cowpea mosaic virus. Chem Biol. 9:813-9 (2002).

Wigand et al., In: Adenovirus DNA, Doerfler, Ed., Martinus Nijhoff Publishing, Boston, pp. 408-441 (1986).

We claim:

1. An infectious adenovirus viral vector particle comprising an adenovirus capsid Fiber protein, comprising the amino acid sequence set forth as SEQ ID NO: 13 and comprising an attachment site for the specific chemical modification of said vector particle, said attachment site comprising the amino acid sequence set forth as SEQ ID NO: 1.

2. The viral vector particle according to claim 1, characterized by at least one solvent-exposed thiol group having an oxidation number of the corresponding sulfur atom being -I.

3. The viral vector particle according to claim 1, dispersed in an oxygen-reduced or oxygen-free buffer optionally supplemented with reducing reagents or in a buffer optionally supplemented with reducing reagents in an atmosphere of Ar.

4. The viral vector particle according to claim 1, further comprising a coupling partner coupled to said attachment site.

5. The viral vector particle according to claim 1, further comprising at least two different coupling partners coupled to said attachment site.

6. The viral vector particle of claim 4, wherein the coupling partner is coupled onto said attachment site via disulfide, thioester, and/or thioether bonds.

7. The viral vector particle according to claim 4, wherein said coupling partner has one or more attachment sites.

8. The viral vector particle according to claim 1, wherein said capsid proteins are chemically modified by chemical reactions not involving thiol groups as reaction partners for the modification reaction.

9. The viral vector particle according to claim 4, whereby said coupling partner(s) is/are cell-specific ligands, polymers, nano gold particles, fluorescence dyes, magnetic substances, or biochemically/catalytically active substances.

10. A nucleic acid molecule encoding an infectious viral vector particle according to claim 1.

11. A method for the generation of an infectious adenovirus viral vector particle comprising the steps:

a) generating an adenovirus viral vector particle according to claim 1 in a packaging cell line;

b) lysing the packaging cells and purifying said viral vector particles in buffers with a pH from 5.0 to 9.0, preferably from 6.8 to 7.4, and more preferably at 7.3, said buffer saturated with atmospheric oxygen and optionally supplemented with reducing reagents, or in oxygen-reduced or oxygen-free buffers optionally supplemented with reducing reagents or in buffers optionally supplemented with reducing reagents in an atmosphere of Ar;

c) contacting coupling partners with said viral vector particles and performing a coupling reaction under formation of a thioether, disulfide, or thioester bond in oxygen-saturated buffers with a pH from 5.0 to 9.0, preferably from 6.8 to 7.4, and more preferably at 7.3, said buffer optionally supplemented with reducing reagents, or in oxygen-reduced or oxygen-free buffers optionally supplemented with reducing reagents or in buffers optionally supplemented with reducing reagents in an atmosphere of Ar.

12. The method according to claim 11, further comprising after step b) or at the same time as or after step c) additional chemical modifications of capsid proteins not involving cysteine residues as a reaction partner.

* * * * *

SEQUENCE LISTING

```
<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide
```

-continued

```
<400> SEQUENCE: 1

Leu Ile Gly Gly Gly Cys Gly Gly Gly Ile Asp
1               5                   10


<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Leu Ile Gly Cys Gly Cys Gly Cys Gly Ile Asp
1               5                   10


<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Leu Ile Cys Cys Cys Cys Cys Ile Asp
1               5


<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4

ttaattggcg gcggatgcgg tggcggcatc gat                                  33


<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5

ttaattggct gcggatgcgg ttgcggcatc gat                                  33


<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6

ttaatttgct gttgttgctg catcgat                                         27


<210> SEQ ID NO 7
<211> LENGTH: 24
<212> TYPE: DNA
<213> ORGANISM: Artificial Sequence
<220> FEATURE:
```

<223> OTHER INFORMATION: Description of Artificial Sequence: Synthetic
Primer

<400> SEQUENCE: 7
tggcggcgga tgcggtggcg gcat 24

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 8
cgatgccgcc accgcatccg ccgccaat 28

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 9
tggctgcgga tgcggttgcg gcat 24

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 10
cgatgccgca accgcatccg cagccaat 28

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 11
ttgctgttgt tgctgcat 18

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 12
cgatgcagca acaacagcaa at 22

<210> SEQ ID NO 13
<211> LENGTH: 592
<212> TYPE: PRT
<213> ORGANISM: Artificial Sequence
<220> FEATURE:
<223> OTHER INFORMATION: Description of Artificial Sequence: Synthetic -continued Peptide

<400> SEQUENCE: 13

```
Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
    50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365

Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asn Asp Lys Leu Thr
385                 390                 395                 400
```

-continued

Leu Trp Thr Thr Pro Ala Pro Ser Pro Asn Cys Arg Leu Asn Ala Glu
405 410 415

Lys Asp Ala Lys Leu Thr Leu Val Leu Thr Lys Cys Gly Ser Gln Ile
420 425 430

Leu Ala Thr Val Ser Val Leu Ala Val Lys Gly Ser Leu Ala Pro Ile
435 440 445

Ser Gly Thr Val Gln Ser Ala His Leu Ile Ile Arg Phe Asp Glu Asn
450 455 460

Gly Val Leu Leu Asn Asn Ser Phe Leu Asp Pro Glu Tyr Trp Asn Phe
465 470 475 480

Arg Asn Gly Asp Leu Thr Glu Gly Thr Ala Tyr Thr Asn Ala Val Gly
485 490 495

Phe Met Pro Asn Leu Ser Ala Tyr Pro Lys Ser His Gly Lys Thr Ala
500 505 510

Lys Ser Asn Ile Val Ser Gln Val Tyr Leu Asn Gly Asp Lys Thr Lys
515 520 525

Pro Val Thr Leu Thr Ile Thr Leu Asn Gly Thr Gln Glu Thr Gly Leu
530 535 540

Ile Gly Gly Gly Cys Gly Gly Gly Ile Asp Asp Thr Thr Pro Ser Ala
545 550 555 560

Tyr Ser Met Ser Phe Ser Trp Asp Trp Ser Gly His Asn Tyr Ile Asn
565 570 575

Glu Ile Phe Ala Thr Ser Ser Tyr Thr Phe Ser Tyr Ile Ala Gln Glu
580 585 590

<210> SEQ ID NO 14
<211> LENGTH: 592
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 14

Met Lys Arg Ala Arg Pro Ser Glu Asp Thr Phe Asn Pro Val Tyr Pro
1 5 10 15

Tyr Asp Thr Glu Thr Gly Pro Pro Thr Val Pro Phe Leu Thr Pro Pro
20 25 30

Phe Val Ser Pro Asn Gly Phe Gln Glu Ser Pro Pro Gly Val Leu Ser
35 40 45

Leu Arg Leu Ser Glu Pro Leu Val Thr Ser Asn Gly Met Leu Ala Leu
50 55 60

Lys Met Gly Asn Gly Leu Ser Leu Asp Glu Ala Gly Asn Leu Thr Ser
65 70 75 80

Gln Asn Val Thr Thr Val Ser Pro Pro Leu Lys Lys Thr Lys Ser Asn
85 90 95

Ile Asn Leu Glu Ile Ser Ala Pro Leu Thr Val Thr Ser Glu Ala Leu
100 105 110

Thr Val Ala Ala Ala Ala Pro Leu Met Val Ala Gly Asn Thr Leu Thr
115 120 125

Met Gln Ser Gln Ala Pro Leu Thr Val His Asp Ser Lys Leu Ser Ile
130 135 140

Ala Thr Gln Gly Pro Leu Thr Val Ser Glu Gly Lys Leu Ala Leu Gln
145 150 155 160

Thr Ser Gly Pro Leu Thr Thr Thr Asp Ser Ser Thr Leu Thr Ile Thr
165 170 175

-continued

```
Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365

Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
            420                 425                 430

Leu Ala Thr Val Ser Val Leu Ala Val Lys Gly Ser Leu Ala Pro Ile
        435                 440                 445

Ser Gly Thr Val Gln Ser Ala His Leu Ile Ile Arg Phe Asp Glu Asn
    450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                485                 490                 495

Phe Met Pro Asn Leu Ser Ala Tyr Pro Lys Ser His Gly Lys Thr Ala
            500                 505                 510

Lys Ser Asn Ile Val Ser Gln Val Tyr Leu Asn Gly Asp Lys Thr Lys
        515                 520                 525

Pro Val Thr Leu Thr Ile Thr Leu Asn Gly Thr Gln Glu Thr Gly Leu
    530                 535                 540

Ile Gly Cys Gly Cys Gly Cys Gly Ile Asp Asp Thr Thr Pro Ser Ala
545                 550                 555                 560

Tyr Ser Met Ser Phe Ser Trp Asp Trp Ser Gly His Asn Tyr Ile Asn
                565                 570                 575

Glu Ile Phe Ala Thr Ser Ser Tyr Thr Phe Ser Tyr Ile Ala Gln Glu
            580                 585                 590
```

<210> SEQ ID NO 15
<211> LENGTH: 590
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 15

```
Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
    50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365
```

-continued

```
Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
            420                 425                 430

Leu Ala Thr Val Ser Val Leu Ala Val Lys Gly Ser Leu Ala Pro Ile
        435                 440                 445

Ser Gly Thr Val Gln Ser Ala His Leu Ile Ile Arg Phe Asp Glu Asn
    450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                485                 490                 495

Phe Met Pro Asn Leu Ser Ala Tyr Pro Lys Ser His Gly Lys Thr Ala
            500                 505                 510

Lys Ser Asn Ile Val Ser Gln Val Tyr Leu Asn Gly Asp Lys Thr Lys
        515                 520                 525

Pro Val Thr Leu Thr Ile Thr Leu Asn Gly Thr Gln Glu Thr Gly Leu
    530                 535                 540

Ile Cys Cys Cys Cys Cys Ile Asp Asp Thr Thr Pro Ser Ala Tyr Ser
545                 550                 555                 560

Met Ser Phe Ser Trp Asp Trp Ser Gly His Asn Tyr Ile Asn Glu Ile
                565                 570                 575

Phe Ala Thr Ser Ser Tyr Thr Phe Ser Tyr Ile Ala Gln Glu
            580                 585                 590
```